United States Patent [19]
Klinkhammer

[11] Patent Number: 5,304,492
[45] Date of Patent: Apr. 19, 1994

[54] SPECTROPHOTOMETER FOR CHEMICAL ANALYSES OF FLUIDS

[75] Inventor: Gary Klinkhammer, Corvallis, Oreg.

[73] Assignee: The State of Oregon Acting by and through the State Board of Higher Education on Behalf of Oregon State University, Eugene, Oreg.

[21] Appl. No.: 798,119

[22] Filed: Nov. 26, 1991

[51] Int. Cl.⁵ .................. G01N 21/64; G01N 21/80
[52] U.S. Cl. .................................. 436/52; 436/84;
436/165; 436/172; 436/805; 422/82.07;
422/82.08; 422/82.09; 250/458.1; 250/461.1;
250/343; 250/373; 356/417
[58] Field of Search ............. 422/82.07, 82.09, 82.08;
436/52, 84, 172, 165, 805; 356/417; 250/461.1,
458.1, 343, 373

[56] References Cited

U.S. PATENT DOCUMENTS

| | | | |
|---|---|---|---|
| 4,488,814 | 12/1984 | Johnson | 356/414 |
| 4,548,907 | 10/1985 | Seitz et al. | 436/163 |
| 4,564,598 | 1/1986 | Briggs | 436/501 |
| 4,650,336 | 3/1987 | Moll | 356/417 |
| 4,676,640 | 6/1987 | Briggs | 356/317 |
| 4,739,171 | 4/1988 | Briggs | 250/459.1 |
| 4,753,530 | 6/1988 | Knight et al. | 356/73 |
| 4,804,849 | 2/1990 | Booth et al. | 250/459.1 |
| 4,929,561 | 5/1990 | Hirsh et al. | 436/116 |
| 4,942,303 | 7/1990 | Kolber et al. | 250/459.1 |
| 4,973,561 | 11/1990 | Hansen et al. | 436/52 |
| 4,983,038 | 1/1991 | Ohki et al. | 356/246 |
| 5,044,747 | 9/1991 | Anthony | 356/246 |
| 5,046,854 | 9/1991 | Weller et al. | 356/440 |

Primary Examiner—James C. Housel
Assistant Examiner—N. Bhat
Attorney, Agent, or Firm—Klarquist, Sparkman, Campbell, Leigh & Whinston

[57] ABSTRACT

An apparatus that conducts in situ analyses of fluids in real time is disclosed. The apparatus comprises bifurcated optic fibers, a pulsed light source, a light detector, a water-tight pressure case that houses the pulsed light source and the light detector, and a flow-through cell that receives one end of each bifurcated optic fiber. The flow-through cell may comprise a plurality of attached tube sections that define a volume which acts as a passageway for conducting fluids. One or more sections of the flow-through cell may be adapted to introduce a reagent into fluid flowing through the cell. Sections of the cell may contain potassium periodate and N,N-diethylaniline that are released into a fluid flowing through the passageway, enabling the spectrophotometer to analyze manganese (II) concentrations by monitoring the decrease in fluorescence accompanying the oxidation of DEA to 2 DEA'. The fluid may also be analyzed by measuring reflectance, absorption, turbidity, and fluorescence.

30 Claims, 6 Drawing Sheets

010
SPECTROPHOTOMETER FOR CHEMICAL ANALYSES OF FLUIDS

ACKNOWLEDGEMENT

This invention was made with support from the Office of Naval Research, contract number N00014-86-K-0325. The government has certain rights in this invention.

FIELD OF THE INVENTION

This invention is directed to an apparatus for in situ analyses of fluids in real time

BACKGROUND OF THE INVENTION

Chemical analyses of fluids, such as natural bodies of water, often involve sample collection and transportation of the sample to a remote test site. Collecting and transporting the sample may alter the sample's composition. For instance, the collection process may contaminate the sample, or a chemical reaction may occur that changes the composition. Collecting and transporting the sample is therefore inefficient, costly, and time consuming.

Moreover, discrete sampling characterizes the state of the fluid only at the time the sample is collected. Natural systems are not static; therefore, the dynamic interactions that occur in natural systems can only be surmised from samples taken at various time intervals.

Remote probes addressed a few of the problems associated with discrete sampling and transportation of the sample to a remote test site. Unfortunately, remote probes are typically limited to measuring gross properties of fluid systems such as temperature, conductivity, and suspended particulate loading.

The advent of fiber optics also addressed limitations apparent in prior analytical devices. For instance, optic fibers convey light to the sample itself, rather than the sample being conveyed to the light source. Furthermore, flexible optic fibers are not limited to specific configurations required in typical laboratory devices. Thus, optic fibers can be configured in transportable devices in manners previously inaccessible.

Bifurcated spectrophotometers are known and have been used to measure various properties of aqueous systems. Many of these devices measure properties of a fluid only through light-scattering or light-absorption techniques. Detecting analytes with light absorption techniques has several disadvantages as compared to detecting fluorescence For instance, the optimum color change associated with an analyte may require lengthy time periods to develop at room temperature, making "real time" measurements impossible. Also, the detection limit of absorption measurements is limited by the extinction coefficient of the colored complex, whereas a fluorescent emission signal can be increased by increasing the excitation energy.

U.S. Pat. No. 4,548,907 describes a bifurcated fiber optic device that includes a multi-wavelength light source and a photomultiplier connected to the light detecting arm. The common end of the optic fibers can be immersed in a fluid sample to measure the fluorescent emissions of a pH sensitive fluorophore. Carbon dioxide levels can also be detected with the device by measuring the pH change associated with the carbon dioxide-bicarbonate ion equilibrium.

Briggs' U.S. Pat. Nos. 4,564,598, 4,676,640, and 4,739,171, describe a bifurcated fiber optic system that measures particulate levels in fluid systems by monitoring fluorescent emissions. These patents also describe a flow tube that houses beads coated with a reagent such as a photosensitive dye.

Knight's U.S. Pat. No. 4,753,530 describes a device intended to be a transportable detecting device for analyzing aqueous media. The bifurcated or trifurcated optic system can measure properties of dilute fluid systems, including turbidity, absorption, reflection, fluorescence and phosphorescence.

The sensitivity and complex nature of typical analytical instruments limit their use to laboratory settings. For instance, spectrophotometers include sensitive electronic equipment and are therefore not suitably immersed in fluids during testing operations Even analytic devices that are compact and transportable require a skilled operator to attain accurate data. Thus, currently available devices are not easily translocated and are susceptible to damage from hostile environments.

Finally, prior art devices typically are designed to measure natural fluorescence rather than induced fluorescence. These devices are therefore limited to detecting species that are themselves capable of fluorescent emissions.

The aforementioned problems make the real time, in situ analyses of fluid systems, such as natural bodies of water, heretofore infeasible.

SUMMARY OF THE INVENTION

The present invention is directed to an apparatus that addresses the limitations identified above. The apparatus comprises a bifurcated zero-angle photon spectrophotometer (ZAPS) probe, a flow-through cell that encloses a common end of the spectrophotometer's bifurcated optic fibers, and a water-tight pressure case that encloses the pulsed light source and the light detector of the spectrophotometer. The apparatus conducts in situ chemical analyses of fluid systems in real time.

The spectrophotometer comprises an excitation fiber and an emission or detection fiber, the common ends of which are housed in the flow-through cell. The pulsed light source generates white light between 200 and 900 nm. An interference filter selects particular wavelengths for transmission through the excitation fiber to the flow-through cell. The detection fiber then conveys emitted fluorescent signals to a photomultiplier tube.

The flow-through cell may comprise a plurality of tubes that are readily attached or detached from one another. The tubes define a passageway for the communication of fluid therethrough. Generally, the flow-through cell includes solid state reagent cartridges that are fluidly connected to a tube housing the common end of the optic fibers. A fluid sample can either flow through the cell or be pumped through the cell as the situation requires.

The solid state reagent cartridges can be readily replaced and are designed for a particular purpose. A specific embodiment of the present invention is directed to analyzing real time manganese (II) concentrations in aqueous solutions. The flow-through cell designed for the manganese (II) analysis comprises two tubes in series The first tube contains a plurality of spherical beads that are coated with $KIO_4$. The aqueous sample flowing past the beads is both filtered and saturated with potassium periodate. The sample thereafter enters the second tube. The second tube has a porous rod therein, the pores of which contain N,N-diethylaniline The aqueous sample, already saturated with potassium periodate, is saturated with N,N-diethylaniline as it flows through the second tube.

Potassium periodate catalyzes the reaction of N,N-diethylaniline and manganese (II) to form 2 DEA'. The aqueous solution, containing 2 DEA', is irradiated in tube 2 which houses the common end of the optic fibers. Irradiation of the sample induces fluorescence of N,N-diethylaniline, which is detected by the emission fiber. The decrease in fluorescence resulting from the formation of 2 DEA' is directly proportional to manganese (II) concentration. The apparatus can analyze the fluid about ten times per second, and can detect manganese (II) concentrations as low as 0.1 nmol/Kg.

The spectrophotometer includes a water-tight pressure case that houses the pulsed light source and photomultiplier tube. The water-tight pressure case protects the spectrophotometer from fluid and pressure damage. Using an appropriate pressure case, the spectrophotometer can be immersed in a fluid up to depths of 6000 meters and can withstand pressures up to about 600 atmospheres. Thus, the present device can effectively conduct oceanographic analysis in real time and in situ.

In addition to measuring induced fluorescence, the present invention is capable of conducting absorption sampling, natural fluorescent sampling and reflective sampling.

Accordingly, a first aspect of the present invention is to provide a spectrophotometer that is relatively insensitive to immersion in a fluid sample up to about 6000 meters.

Another aspect of the present invention is to provide an invention capable of conducting in situ analyses of natural bodies of water in real time.

Another aspect of the present invention is to provide a flow-through cell comprising a plurality of fluidly connected tubes that can be used to detect vanishingly low levels of specific trace elements such as manganese (II) in aqueous systems by measuring induced fluorescence.

DETAILED DESCRIPTION OF THE INVENTION

General Construction Operation

Figure 1:
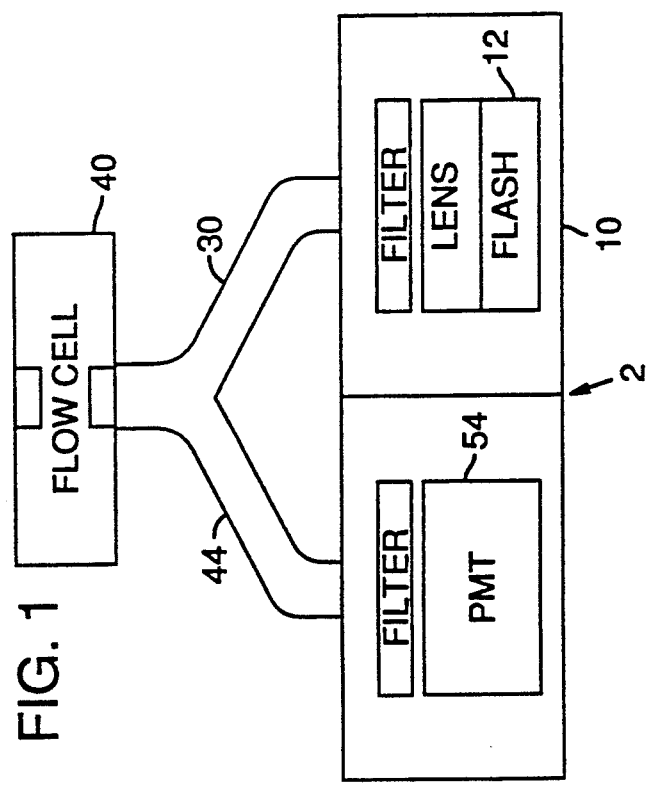
FIG. 1 is a schematic diagram of a ZAPS probe and flow-through cell according to the present invention.

FIG. 1 shows a block diagram of the present invention. The invention comprises a zero-angle photon spectrophotometer (ZAPS) 2, the sensitive electronic portions of which are housed in a water-proof pressure case 10. A xenon flash tube 12 initiates white light. This light is monochromated and focused on an excitation optic fiber 30. Optic fiber 30 transmits the filtered light to a flow-through cell 40 that houses a common end of the excitation fiber 30 and emission fiber 44.

A fluid sample flowing through the flow-through cell 40 may be saturated with a variety of reagents that make it possible, through induced fluorescence, to determine the concentration of a particular analyte of interest. A preferred embodiment of the invention is used to determine manganese (II) concentrations. The emission fiber 44 detects the induced fluorescence of analytes contained in the fluid following irradiation of the fluid sample in the flow-through cell 40. Emission fiber 44 conveys the detected signal back to the water-proof case 10 where it is again filtered. The detected fluorescence is converted to a current that is amplified by a photomultiplier tube 54. This signal is then converted into a frequency signal that can be telemetried to a remote receiving station.

ZAPS Probe

Figure 2:
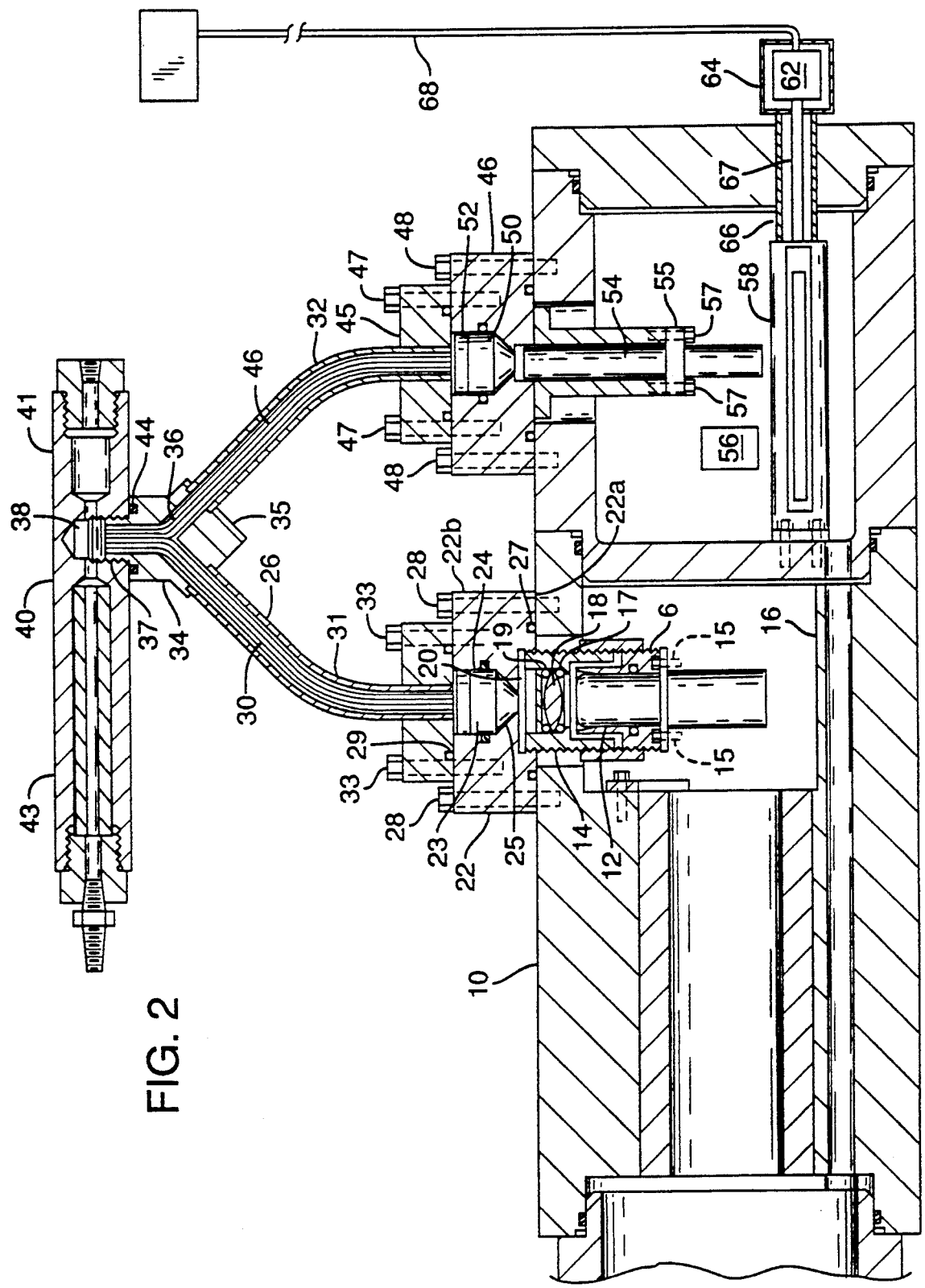
FIG. 2 is a more detailed schematic view of the ZAPS probe and the flow-through cell shown in FIG. 1.

FIG. 2 illustrates the spectrophotometer 2 and flow-through cell 40 in greater detail. Portions of the electronic assembly comprising the ZAPS probe 2 are housed in water-proof pressure case 10. The illustrated pressure case 10 comprises a block of anodized aluminum that is machined to receive various components of the spectrophotometer 2. Pressure case 10 can withstand pressures of about 600 atmospheres and can be immersed in a fluid, such as ocean water, up to a depth o f approximately 6,000 meters while protecting the spectrophotometer 2 from fluid and pressure damage.

Flash assembly 6, housed inside pressure case 10, comprises a pulsed light source such as xenon flash tube 12, a flash tube socket 14, and a power supply 16 Socket 14 is bolted to pressure case 10 with attachment bolts 15. Socket 14 permits axial adjustments of the flash tube 12 for focusing with focusing lens 18. Flash tube 12 may be any suitable light source known in the art capable of emitting pulsed-light from about 200 nm to about 900 nm. A preferred flash tube is a 20 mm gap xenon lamp from the Hamamatsu Corporation of Japan, Model No. L2467. Flash tube 12 is powered by power supply 16 which operates at an applied voltage of about 28 volts, and a flash lamp trigger voltage of about 12 volts. A preferred power supply is P5350 power supply made by EG&G Corporation of Salem, Mass.

Power supply 16 triggers a pulse of light from the flash tube 12. The light is focused onto an excitation fiber 30 by lens 18. Lens 18 may be any suitable lens known in the art. A preferred embodiment of lens 18 is a one inch diameter fused-silica lens made by the Oriel Corporation of Stratford, Connecticut, Model No. 39311. Lens 18 has a focal length of about 20 mm. Lens 18 is positioned above the flash tube 12 inside a machined region of the pressure case 10. Lens 18 is held firmly in place by a pair of O-rings 17, 19.

The light emerging from flash tube 12 is white light having wavelengths between about 200 nm to about 900 nm. A particular wavelength of light is selected from the white light produced by the flash tube 12 by an interference filter 20. The wavelength of interest may vary according to the particular analytical test of interest. A preferred embodiment of the present invention requires excitation light of 310 nm. Thus, a preferred interference filter 20, capable of selecting a wavelength of 310 nm, is a 1 inch interference filter manufactured by the Oriel Corporation, Model No. 53375. One skilled in the art will realize that the interference filter 20 can be any suitable filter known in the art. Filters can be changed to select wavelengths between about 200 nm and 900 nm.

To make it easy to change from one interference filter to another, the filter 20 is housed inside a stainless steel member 22. Member 22 is substantially cylindrical and has two major opposed surfaces 22a, 22b. Member 22 is bolted to the pressure case 10 with attachment bolts 28. Member 22 includes channel 23 therethrough into which a quartz window 24 is inserted. Quartz window 24 has a substantially cubical portion and a truncated pyramid portion 25. The member 22 is machined to exactly accommodate the shape and dimensions of quartz window 24. The illustrated quartz window 24 was manufactured by Optics for Research of New Jersey. A small amount of vacuum grease may be applied to the outer surface of quartz window 24 to ensure a proper seal as the pressure increases when pressure case 10 is immersed below the surface of a fluid. Member 22, housing interference filter 20 and quartz window 24, is bolted to the outside of the pressure case 10 with attachment bolts 28. Thus, an operator can change the interference filter 20 simply by removing the attachment bolts 28.

An O-ring 27 is positioned between a first surface 22a of member 22 and pressure case 10. An O-ring 29 separates the surface 22b from cylindrical member 31. Member 31 is bolted to member 24 with attachment bolts 33. A stainless steel fiber optic guide channel 24 is welded to cylindrical member 31.

The light monochromated by interference filter 20 is communicated by excitation fiber 30 to a light-cell cavity 38. Excitation fiber 30 is typically a fused-silica optic fiber. A preferred excitation fiber 30 is made by Polymicro Company of Tempe, Arizona, Model No. FHP 500/550/580. The fused-silica fiber 30 is clad with a plastic material. The fused silica fiber 30 is positioned inside optic fiber conduit 26 and is firmly fixed therein with an epoxy. Optic fiber conduit 26 is made from stainless steel and has a 0.5 inch outer diameter and a 0.09 inch thick wall. The epoxy used to seal fiber 30 in conduit 26 is a general purpose epoxy made by Tap Plastics Company of Portland, Oreg. The ends of the fused silica fiber 30 are then cut and polished with polishing papers supplied by the Buehler Corporation of Lake Bluff, Ill.

Optic fiber conduits 30 and 32 are welded to a stainless steel member 34. Member 34 has a substantially rectangular body, a diamond-shaped receiving end 35, and a threaded end 37. Member 34 has a y-cavity 36 that acts as a guide channel for excitation fiber 30 and detection fiber 46. Thus, excitation fiber 30 extends from guide conduit 24 into and through the y-cavity 36.

The polished tips of excitation fiber 30 and emission fiber 46, arranged in a random pattern, terminate in light-cell cavity 38. The light-cell cavity 38 has a fixed volume and consists of a ⅜ inch threaded cavity that extends about 0.5 inch into the side of flow-through cell 40. Flow-through cell 40 comprises a solid, substantially cylindrical member of black, ultra high molecular weight (UHMW) plastic material Although the size of the flow-through cell 40 is not critical, a preferred length is about 6 inches with a diameter of about one inch. The preferred embodiment of flow-through cell 40 has a short end 41, having a length of about 2 inches, and a long end 43 having a length of about 4 inches. The midpoint of cavity 38 is positioned about 2 inches from the short end 41. The inner walls of cavity 38 are threaded to receive threaded end 37 of member 34. O-ring 44 ensures a leak-proof seal at the interface of the flow-through cell 40 and the member 34.

The monochromated light exiting excitation fiber 30 irradiates a fixed volume of fluid sample flowing through light-cell cavity 38. Emission fiber 44, which is identical to the fused silica fiber 30 discussed above, detects either the induced fluorescence or the ambient fluorescence of an analyte contained in the fluid sample flowing through cell cavity 38.

Emission fiber 44 is housed in stainless steel optic fiber conduit 32 that is substantially identical to conduit 30. Emission fiber 44 is held firmly inside the guide channel 32 by a waterproof epoxy. Emission fiber conduit 32 is connected to a substantially cylindrical member 45 that is of the same construction as cylindrical member 31. Cylindrical member 45 is bolted to member 46 using attachment bolts 47. Member 46 is attached to pressure case 10 with attachment bolts 48. Member 46 has a passageway machined therethrough that receives quartz window 50 in the same manner as member 22 receives quartz window 23.

Member 46 also houses interference filter 52. Interference filter 52 is also made by the Oriel Corporation. A preferred embodiment of ZAPS probe 2 monitors emission wavelengths of about 350 nm. The signal emerging from emission fiber 46 thus passes through filter 52 which selects an excitation wavelength of 350 nm.

After passing through interference filter 52, the emission signal is received by photomultiplier tube (PMT) 54, that is itself housed in pressure case 10. Photomultiplier tube 54 may be any photomultiplier used in the art. However, a preferred embodiment of PMT 54 of the present invention is made by the Hamamatsu Corporation, Model No. R760. Photomultiplier 54 is held firmly in place by spacer 55 that is bolted to pressure case 10 with attachment bolts 57. Photomultiplier 54 comprises an ends-on tube that is positioned in direct contact with the quartz window 50 by adjusting spacer 55. The photomultiplier 54 has a bias voltage of about −1000 volts. This bias voltage is supplied by a Hamamatsu power supply 56, Model No. C1309-04. PMT 54 produces a current that has a typical amperage of about one microamp.

The output from PMT 54 is a current that is directly proportional to the number of photons impinging on the cathode. The signal produced by the PMT 54 is captured with a fast-response pre-amp circuit 58 located at the base of the PMT 54. Pre-amp circuit 58 converts the current pulses from the PMT 54 to voltage pulses. The voltage pulses from the pre-amp circuit 58 are of negative polarity, are about 10 microseconds in duration, and can include noise from the flash tube 12. The signal from the pre-amp circuit 58 signal is sent to a sample/-hold amplifier circuit (not shown) which isolates the signal from the noise, integrates the signal to produce a continuous DC output, inverts the polarity, and amplifies the signal to produce a 0 to +5 volt output. The amplification circuit 60 contains a sample hold chip, a timing switch, and a delay circuit. The delay circuit delays integrating the emission signal for a period of about 20 microseconds. This delay allows any noise produced by the flash tube 12 to pass. The emission signal is then integrated for a period of about 20 microseconds.

The signal from the amplifier circuit is sent out of the pressure case 10 to an A/D converter 62. Converter 62 is typically located in a pressure bottle 64 that is connected to pressure case 10 by conduit 66. Conduit 66 houses power cable 67 that connects the amplifier circuit and A/D converter 62. The A/D converter 62 converts the DC output to a digitized frequency and telemetries the digitized frequency to a remote site such as a ship through conducting cable 68. A/D converter 62 is a standard piece of oceanographic equipment originally developed to process conductivity/temperature/density data. The A/D converter 62 can handle data from at least six or more external probes simultaneously. The A/D converter 62 may be any converter known in the art. A preferred embodiment of A/D converter 62 is produced by Seabird Electronics of Seattle, Washington, Model No. SBE9-02

Flow-Through Cell

Figure 3:
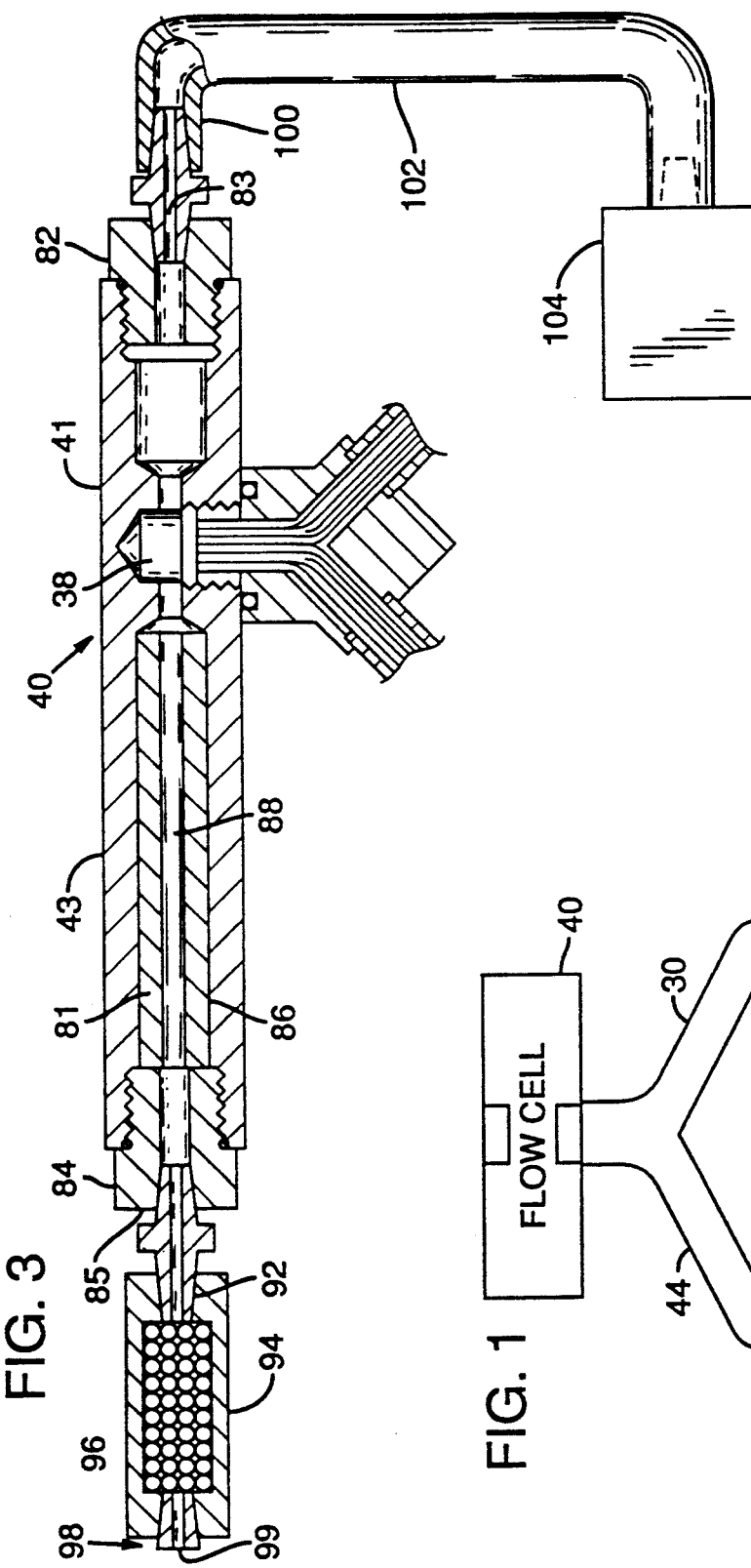
FIG. 3 is a schematic view of the flow-through cell of FIG. 2.

With reference to FIGS. 2 and 3, the ZAPS probe 2 can be used in conjunction with flow-through cell 40. The flow-through cell 40 may comprise a plurality of connected, but readily detachable, tubes. The number of tubes can vary and depends upon the particular application in question.

A preferred embodiment of flow-through cell 40 as illustrated in FIG. 3 is used for the detection of manganese (II). Flow-through cell 40 comprises a cylinder of UHMW plastic material The short end 41 and the long end 43 of flow-through cell 40 are threaded to receive caps 82 and 84 respectively. Caps 82 and 84 are made of teflon and define ports 83 and 85, respectively, through which a fluid may flow. Caps 82 and 84 extend into the ends of flow-through cell 40 about 0.8 inch.

Flow-through cell 40 has a passageway 81 that extends therethrough. The diameter of passageway 81 is approximately 0.57 inch for approximately 4.6 inches as measured from long end 43. Passageway 81 then constricts to a diameter of about 0.12 to about 0.13 inch immediately before and after light-cell cavity 38. The diameter of passageway 81 thereafter increases to about 57 inch as it extends through short end 41 of flow-through cell 40.

Passageway 81 has a constant diameter as it extends into long end 43 about 4.6 inches. This region of passageway 81 is sized to receive a porous rod 86. Porous rod 86 is made from an extruded, high porosity fluorocarbon (PTFE) and is sized to exactly fit the passageway 81. Porous rod 86 is first soaked in N,N-diethylaniline before it is positioned in the passageway 81. Porous rod 86 is sealed inside passageway 81 by screwing cap 84 in place. Porous rod 86 includes a channel 88 therethrough that has a diameter of about 0.12 to about 0.13 inch. A fluid sample flows through channel 88 and into light-cell cavity 38.

Port 85 is threaded to receive threaded fitting 92. Threaded fitting 92 is sized to receive a second cartridge 94. Cartridge 94 is substantially cylindrical and is made out of acrylic. The cartridge 94 is initially produced as a solid acrylic cylinder that is hollowed out to receive beads 96 therein. The hollowed-out portion of cartridge 94 is substantially completely filled with spherical beads 96. Cap 98 is screwed into cartridge 94 to retain beads 96 therein.

Beads 96 are made of a fast-curing acrylic. The purpose of the beads 96 is two-fold: first, they filter the fluid sample that flows through the cartridge 94; second, beads 96 are used to introduce a reagent into the fluid flowing past beads 96. A preferred embodiment of the beads 96 is used to introduce potassium periodate into a fluid flowing through cartridge 94. Bead 96 is produced by mixing five parts by weight of a two-component acrylic with one part solid potassium periodate. The potassium periodate may either be sprinkled onto the mixture or mixed therein. The mixture is then drawn into a pipette such as a 9-inch glass disposable pipette. The mixture is then forced out of the pipette to form a spherical bead 96 having a diameter of about 3 mm. The beads 96 are then allowed to cure. Beads 96 are retained inside cartridge 94 by screwing cap 98 into cartridge 94. Cap 94 has a port 99 through which fluid enters cartridge 94.

The short end 41 of flow-through cell 40 has a cap 82 therein. Cap 82 includes a hose connection 100 that can receive a hose 102 extending from a pump 104. Pump 104 may be any pump known in the art. However, a preferred pump is an SBE-5-02 pump produced by Seabird Electronics of Seattle, Wash. Pump 104 moves a fluid sample through the flow-through cell 40 and ensures that the residence time of the sample in the flow-through cell 40 is constant. The residence time is on the order of 5 seconds.

Operation

The ZAPS probe 2 is capable of making a number of measurements, including absorption, reflectance, induced fluorescence and natural (ambient) fluorescence. Absorption applications usually require a chemical reaction between selected reagents to produce a chromophore (a molecular group capable of selective light absorption that results in coloration). The product of the reaction typically absorbs light strongly and thus has a high molar absorptivity at a particular wavelength within the visible region. The molar absorptivity of the product and the cell path length limit the sensitivity of absorption processes. Thus, though the ZAPS probe 2 can be used to carry out absorption experiments such as the detection of Iron (III) described below (see FIG. 4), fluorescence measurements are typically of greater sensitivity.

Figure 4:
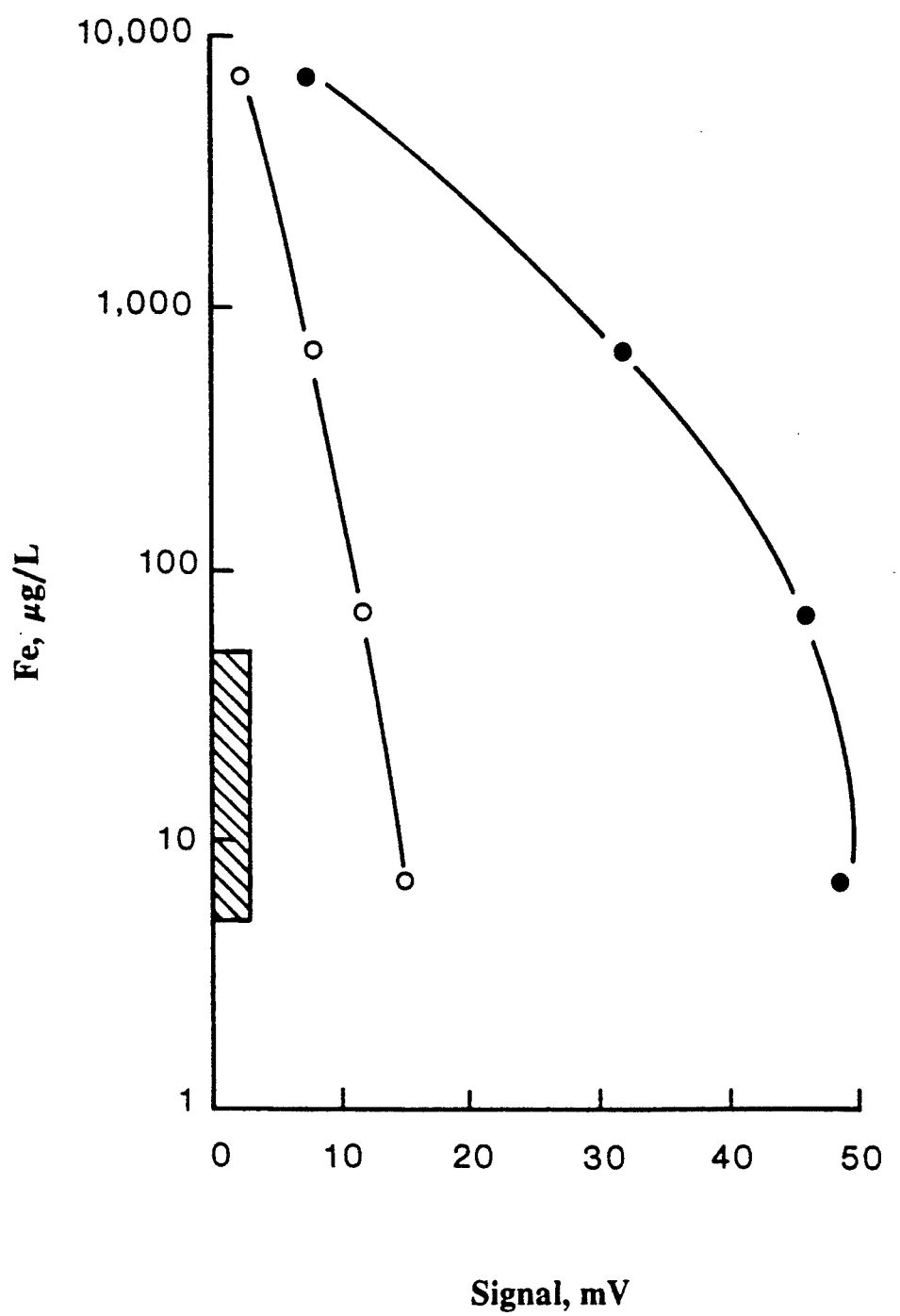
FIG. 4 is a standard curve of the concentration of Fe (III) versus absorption signal strength produced by the absorption of Fe(III) at 310 nm following pH induced flocculation.

The data shown in FIG. 4 was obtained by irradiating sea water samples at 310 nm with the ZAPS probe 2. The Fe (III) and the Fe (II) chloride complex has a molar absorptivity of about 2,500 molar absorbance units/molar centimeter that absorbs in the near ultraviolet region. The absorption of a sample containing the Fe (III)-Fe (II) chloride complex (sea water) can be compared to a standard absorption curve to measure the concentration of iron in the aqueous sample. The absorption of the Fe (III)-Fe (II) chloride complex is linear with concentration over a range of 7–7000 $\mu$g/liter. These concentrations are within the dissolved iron concentrations of natural bodies of water.

The ZAPS probe 2 can also be used to make reflectance measurements. A particular application of reflectance is the determination of the turbidity of a fluid. Prior nephelometry devices illuminate a sample with white light, which is thereafter collected at an angle from the source. The collection angle is usually 90°.

Illuminating a sample with the monochromated light of the ZAPS probe 2 results in scattering measurements that are more sensitive than previously could be obtained using prior devices. For instance, FIG. 4 illustrates results obtained when using the ZAPS probe 2 as a zero-angle reflectometer. A reflectometer is the appropriate term when scattering measurements are made with monochromatic light. In order to test the ZAPS probe 2 as a reflectometer, the pH of sea water containing dissolved iron was adjusted slightly upward. The solution was then illuminated with monochromatic light from the ZAPS probe 2. The data presented in FIG. 4 indicates that the ZAPS probe 2 response is substantially linearly related to concentration. These measurements would be useful in monitoring the stability and clarity of the fluids within drill holes.

The ZAPS probe 2 is capable of detecting fluorescence at levels which are lower than commercially available deep-sea fluorometers. Commercially available instruments generally use a monochromated light that is neither focused nor collimated. As a result, much of the light is either absorbed or scattered. The ZAPS probe 2 eliminates problems associated with prior art devices by focusing the output of flash tube 12 onto the polished end of excitation fiber 30. Excitation fiber 30 thereafter transmits an intense pulse of monochromatic light to light-cell cavity 38.

Figure 5:
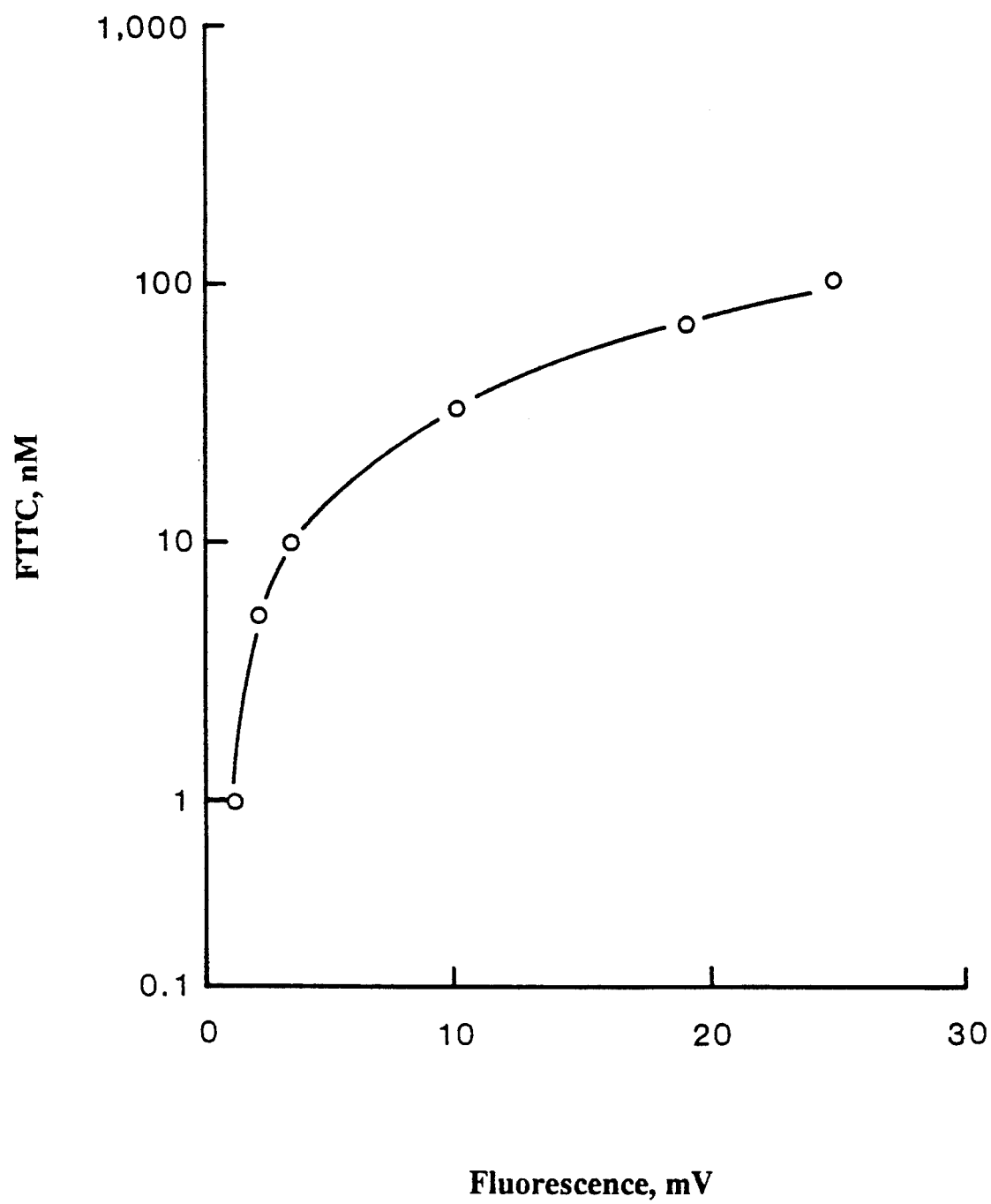
FIG. 5 is a standard curve illustrating the fluorescence of fluorescein isothiocyanate.

FIG. 5 illustrates fluorescence data obtained with the ZAPS probe 2 for dilute solutions of fluorescein isothiocyanate. Fluorescein isothiocyanate has a molar absorptivity similar to chlorophyll Chlorophyll is used as a standard for determining the sensitivity of commercial devices. The ZAPS probe 2 was used to detect the level of fluorescein isothiocyanate in dilute solutions. The results illustrated in FIG. 5 indicate that the detection limit of a single excitation and emission fiber is on the order of at least 1 nmol/Kg, which is similar to the chlorophyll detection limits of commercially available instruments.

The sensitivity of the fluorescence method is enhanced relative to absorptivity measurements simply by balancing the amount of excitation energy (increased luminous flux, increases sensitivity) and the effects of stray light. The sensitivity of the ZAPS probe 2 can be increased to a level capable of detecting dissolved organics.

The sensitivity of the ZAPS probe 2 and the capability to detect dissolved organics has many useful applications. For instance, hydrocarbon deposits sometimes leak out of marine sediments when the deposit occurs near enough to the sea/sediment interface. This phenomenon has led to exploration techniques that monitor dissolved organic carbon (DOC) anomalies in shelf waters to locate underlying oil deposits. The ZAPS probe 2 can be used to develop three-dimensional maps of the hydrocarbon emissions of the sea floor. This is only possible since the ZAPS probe 2 is capable of immersion in the ocean up to about 6,000 meters without affecting the ability of ZAPS probe 2 to produce data in real time.

The sensitivity of the spectrophotometer may also prove useful in dye experiments One example might be where a one hole/two dye experiment is employed. For instance, inert dyes might be injected at various de into drill holes containing ground water. The dye concentrations could be monitored by an array of down-hole sensors patterned after the ZAPS probe 2.

Figure 6:
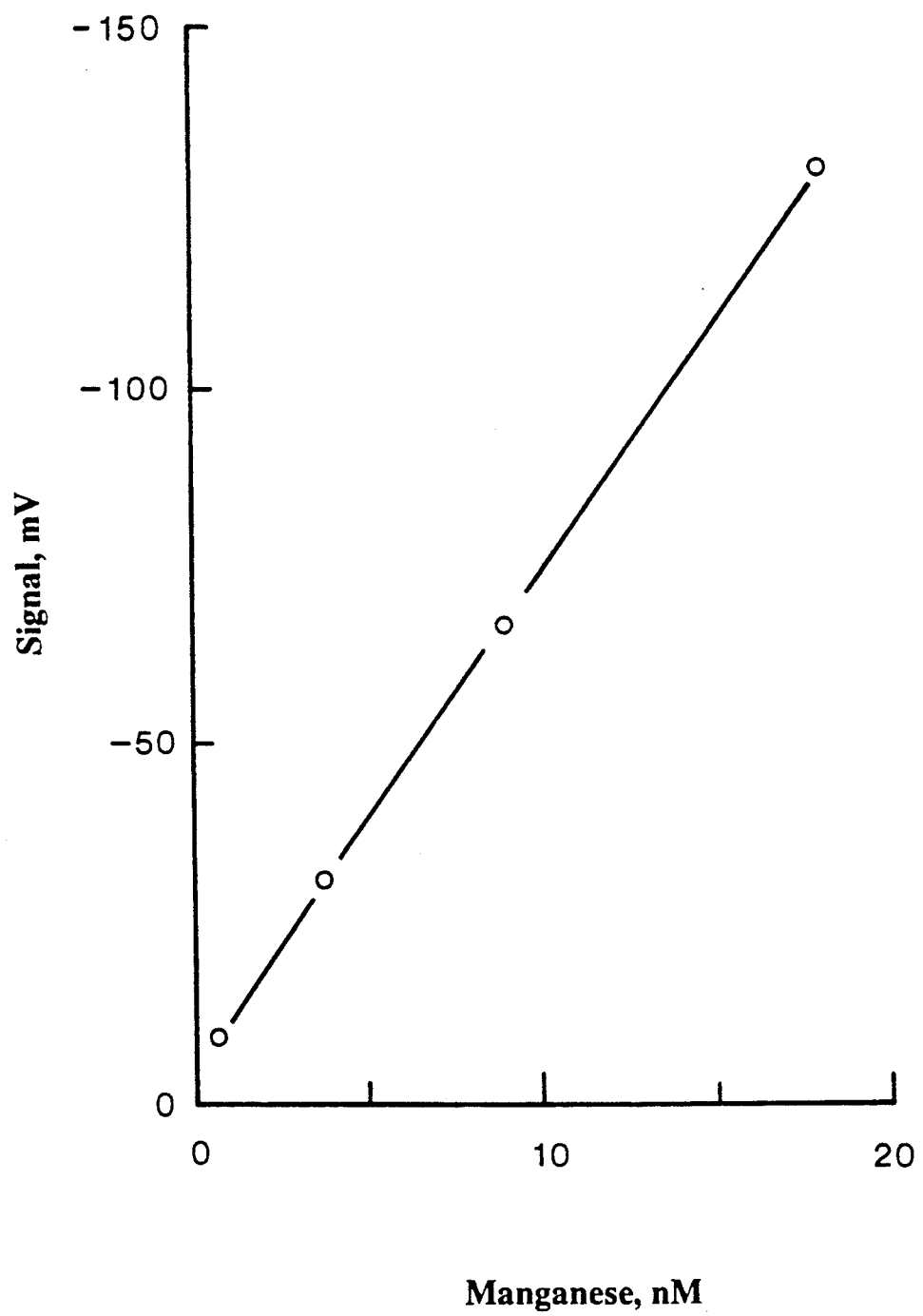
FIG. 6 is a standard curve for the concentration of manganese in sea water produced using the ZAPS probe.

A preferred embodiment of ZAPS probe 2 is used to conduct fluorescent experiments to detect inorganic substances that react with weakly fluorescent organic compounds. FIG. 6 is a standard curve for the concentration of manganese in sea water produced with the ZAPS probe 2. This curve was obtained by combining solid state reagent chemistry with the spectrophotometric capabilities of the ZAPS probe 2. Particularly, the probe 2 and flow-through cell 40 can be used to detect manganese (II) concentrations.

DEA is weakly fluorescent in aqueous systems. N,N-diethylaniline (DEA), when exposed to light of an appropriate wavelength, namely 310 nm, produces a fluorescent emission at a wavelength higher than 350 nm. The oxidation product of DEA and manganese (II) is 2 DEA' (see reaction below) which is not fluorescent at these wavelengths. DEA is reduced to 2 DEA' by manganese (II); manganese (II) is oxidized to manganese (IV). This reaction allows the ZAPS probe 2 to detect the decrease in the fluorescence of DEA as it is converted to 2 DEA'. Minute quantities of manganese (II) can be detected by this method. The detection limit of the ZAPS probe 2 has been determined to be at least as low as 0.1 nmol/Kg. The oxidation reaction is relatively slow. Therefore, potassium periodate ($KIO_4$) is used to catalyze the oxidation reaction.

Oxidation-Reduction Reaction of Mn (II) and DEA

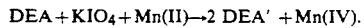

$DEA + KIO_4 + Mn(II) \rightarrow 2\ DEA' + Mn(IV)$.

When manganese (II) is present in the solution entering cartridge 94, it reacts with dissolved DEA. This reaction is catalyzed by potassium periodate and produces 2DEA'. The reaction is relatively fast so that the solution entering light-cell cavity 38 contains 2 DEA'.

The aqueous solution flowing through light-cell cavity 38 is illuminated with excitation light of 310 nm by excitation fiber 30. DEA absorbs excitation light of 310 nm and produces a fluorescent emission at about 350 nm. 2 DEA' is not fluorescent. Thus, the decrease in fluorescent emissions is proportional to the Mn (II) concentration. The data obtained by the ZAPS probe 2 can be used to develop a standard curve for the concentration of manganese (II) ion in sea water. FIG. 6 illustrates a standard curve for manganese concentration for sea water produced with the ZAPS probe 2.

Figure 7:
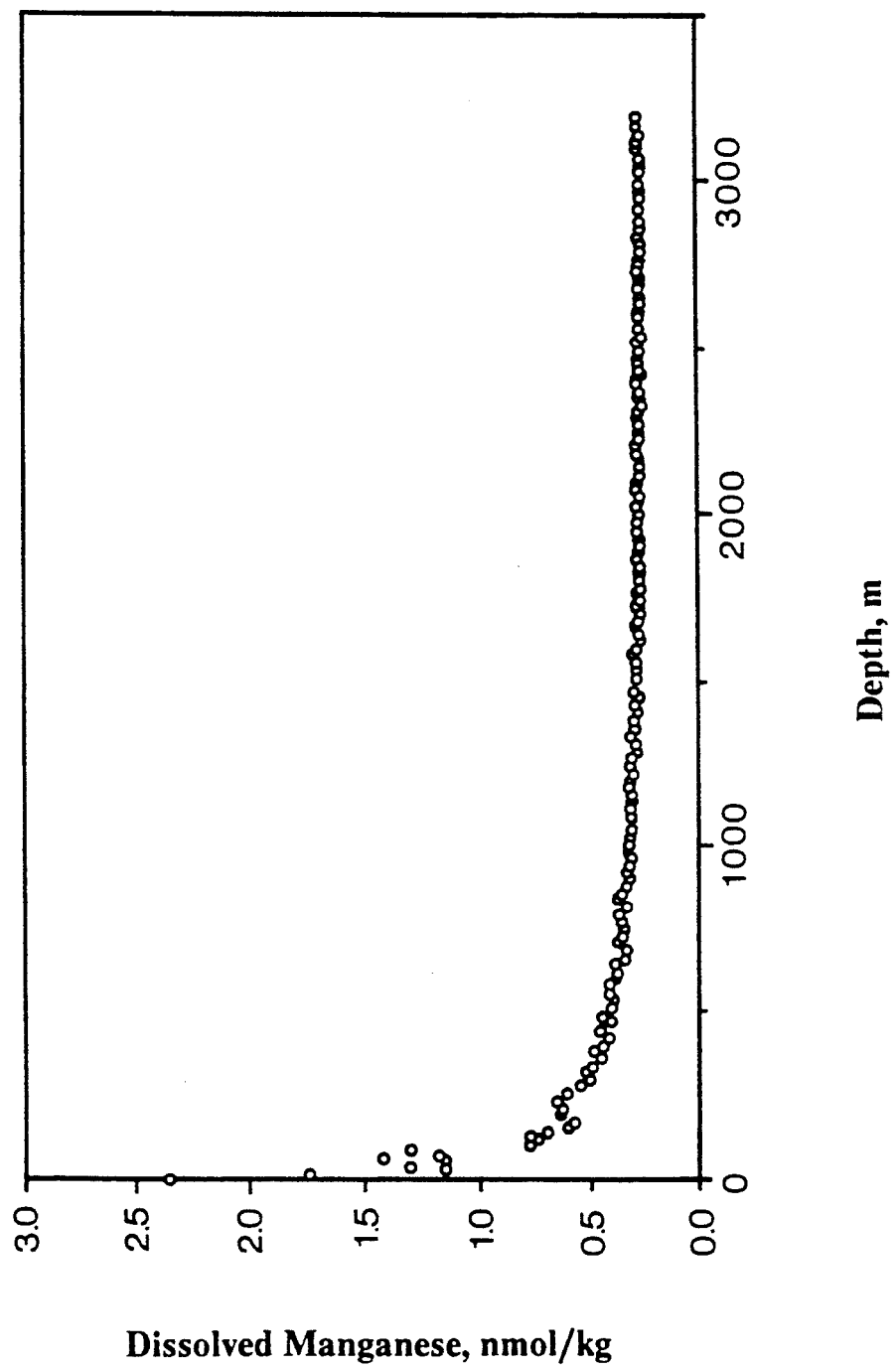
FIG. 7 is a plot of manganese concentration versus ocean depth made in situ and in real time with the ZAPS probe. The plot indicates that the manganese concentration becomes monotonic at 0.27 nmol/Kg below 1200 meters.

The ZAPS probe 2 can also be used to determine the concentration of manganese versus ocean depth. FIG. 7 illustrates data that was obtained in situ and in real time using the ZAPS probe 2. This data is consistent with the geochemistry of manganese and its distribution in the oceans as determined heretofore. The data in FIG. 7 indicates that the ZAPS probe is capable of detecting manganese concentrations at exceedingly low levels, approaching 0.1 nmol/Kg $H_2O$.

Having described a preferred embodiment of the invention, it should be understood by one skilled in the art that one can deviate from the preferred elements of the invention and still be within the concept of the invention described herein.

We claim:

1. A method for detecting and quantifying the amount of manganese (II) ion contained in a fluid, the method comprising the steps of:

(a) immersing an analytical device in a fluid wherein the analytical device comprises a pulsed light source, a light detector, first and second bifurcated optic fibers, and a flow-through cell comprising a plurality of tubes removably attached to each other and defining a volume which acts as a passageway to conduct a stream of fluid, the first optic fiber transmitting light from the pulsed light source to the flow-through cell, and the second optical fiber transmitting light emitted in the flow-through cell to the detector;

(b) passing a stream of the fluid through a potassium periodate such that potassium periodate is transferred to the fluid;

(c) passing the fluid which results from step (b) through a second tube which contains a source of N,N-diethylaniline such that N,N-diethylaniline is transferred to the fluid;

(d) irradiating the fluid which results from step (c) with excitation light; and (e) comparing the intensity of the fluorescent light emission detected in the flow-through cell following oxidation of the N,N-diethylaniline by manganese (II) to the intensity of a standard fluorescent signal for the fluid containing just N,N-diethylaniline to determine the decrease in fluorescent intensity; and (f) converting the decrease in intensity of the fluorescent signal to a manganese (II) ion concentration.

2. A method according to claim 1 including the step of pumping the fluid through the passageway.

3. The method according to claim 1 wherein the fluid is irradiated with excitation light of 310 nm and the fluorescent emission of the oxidized N,N-diethylaniline is measured at 350 nm.

4. A method according to claim 1 wherein the first fluid is sea water.

5. A method of analyzing fluids in situ and in real time comprising:

immersing an analytical device in a fluid wherein the analytical device comprises a pulsed light source, a light detector, a water-tight pressure case that houses the pulsed light source and the light detector, a flow-through cell comprising a plurality of tubes that are removably attached to each other and which define a volume that acts as a passageway to conduct a stream of fluid, and first and second bifurcated optic fibers, the first optic fiber transmitting light from the pulsed light source to the flow-through cell, and the second optic fiber transmitting light emitted in the flow-through cell to the detector;

flowing the fluid through at least one of the plurality of tubes such that the fluid contacts at least one reagent housed in the plurality of tubes in such a manner that the reagent(s) react with one or more particular analytes carried by the fluid;

after the flowing, irradiating the fluid with excitation light; and determining the intensity of fluorescent light emitted from the fluid.

6. A method according to claim 5 wherein the fluid is irradiated at least ten times per second.

7. A method according to claim 5 wherein the analyte is manganese (II).

8. An apparatus for analyses of fluids comprising:
a flow-through cell;

a spectrophotometer comprising a pulsed light source, a detector, and first and second bifurcated optic fibers, the first optic fiber transmitting light from the pulsed light source to the flow-through cell, and the second optic fiber transmitting light emitted in the flow-through cell to the detector; and a water-tight pressure case that houses the pulsed light source and the detector.

9. An apparatus according to claim 8 wherein the pressure case is of sufficient strength to be immersed in a fluid to a depth of up to about 6000 meters and withstand pressures of about 600 atmospheres while protecting the pulsed light source and detector from pressure and fluid damage.

10. An apparatus according to claim 8 including excitation and emission filters associated with the first and second optic fibers respectively for selecting a particular wavelength of light wherein the excitation and emission fibers are housed in a container that is readily attached to or detached from the pressure case.

11. An apparatus according to claim 10 wherein the excitation filter selects a wavelength of 310 nm and the emission filter selects a wavelength of 350 nm.

12. An apparatus according to claim 8 wherein the flow-through cell comprises a plurality of tubes, each tube including attachment means for quickly attaching or detaching a tube from another of the tubes, the tubes together defining a volume which acts as a passageway to conduct a stream of fluid.

13. The apparatus according to claim 12 wherein each tube of the plurality of tubes contains a different reagent that dissolves or becomes suspended in fluid flowing through the passageway.

14. An apparatus according to claim 13 wherein the flow-through cell comprises a first tube and a second tube, wherein the second tube encloses a porous rod adapted to release N,N-diethylaniline into the fluid flowing through the passageway, and the first tube contains a filter for filtering fluid flowing to the second tube.

15. An apparatus according to claim 16 wherein the filter is adapted to release potassium periodate into fluid flowing past the filter.

16. An apparatus according to claim 15 wherein the filter comprises beads made of a plastic material.

17. An apparatus according to claim 8 wherein the pulsed light source generates light wavelengths of from about 200 nm to about 900 nm.

18. An apparatus according to claim 8 wherein the spectrophotometer is adapted to analyze in situ the fluid flowing through the flow-through cell about ten times per second.

19. An analytical device for determining manganese (II) concentrations in fluids comprising:

a flow-through cell comprising a plurality of tubes that are removably attached to each other, the tubes together defining a volume which acts as a passageway to conduct a stream of fluid, the tubes housing at least one reagent that dissolves or is suspended in the fluid conducted through the passageway;

a spectrophotometer comprising a pulsed-light source, a light detector, and bifurcated first and second optic fibers, the first optic fiber transmitting light to the flow-through cell and the second optic fiber transmitting light emitted in the flow-through cell to the detector; and a water-tight pressure case that houses the pulsed light source and the light detector.

20. A device according to claim 19 wherein the flow-through cell comprises a first tube containing a plurality of beads that are adapted to release potassium periodate into the fluid flowing past the beads, and a second tube that is adapted to release N,N-diethylaniline into the fluid flowing through the second tube.

21. An apparatus according to claim 20 wherein the device is sufficiently sensitive to detect fluorescent signals corresponding to manganese (II) concentrations as low as about 0.1 nmol/Kg.

22. An apparatus according to claim 19 wherein the water-tight pressure case can be immersed in a fluid up to about 6000 meters and can withstand pressures of about 600 atmospheres while protecting the pulsed light source and detector from fluid and pressure damage.

23. An apparatus according to claim 19 including pumping means for moving a fluid through the flow-through cell.

24. An apparatus for analyzing fluids, comprising:
 a spectrophotometer comprising a pulsed light source, a light detector and first and second bifurcated optic fibers, the first optic fiber transmitting light from the light source to a sampling area, and the second optic fiber transmitting light emitted in the sampling area to the detector; and
 a water-tight pressure case that houses the pulsed light source and the detector.

25. An apparatus according to claim 24 wherein the water-tight pressure case protects the pulsed light source and light detector from immersion in the fluid up to about 6000 meters.

26. An apparatus according to claim 24 wherein the apparatus is adapted to analyze a fluid in situ about ten times a second.

27. An apparatus for measuring real time manganese (II) ion concentration in water comprising:

a flow-through cell comprising a first and second tube, the first and second tubes being removably attached to one another and defining a volume which acts as a passageway to conduct water, the first tube containing a plurality of beads adapted to release potassium periodate into the water flowing through the passageway, and the second tube adapted to release N,N-diethylaniline into the water flowing through the passageway;
 a spectrophotometer comprising a pulsed light source, a light detector and first and second bifurcated optic fibers, the first optic fiber transmitting light from the pulsed light source to the flow-through cell, and the second fiber transmitting light emitted in the flow-through cell to the detector;
 a water-tight pressure case that houses the pulsed light source and the light detector;
 communication means that link the apparatus to a control center; and
 control means located in the control center for sending, receiving and interpreting signals from the apparatus.

28. An apparatus according to claim 27 including excitation and emission filters associated with the first and second bifurcated optic fibers respectively, the excitation filter selecting light of 310 nm and the emission filter selecting light of 350 nm, the excitation and emission fibers housed in a container that is readily attached to or detached from the pressure case.

29. An apparatus according to claim 27 wherein the water-tight pressure case can protect the pulsed light source and light detector from fluid and pressure damage when immersed into water up to about 6000 meters.

30. An apparatus according to claim 27 that is sufficiently sensitive to detect fluorescent signals corresponding to manganese (II) concentrations at least as low as 0.1 nmol/Kg.

* * * * *

UNITED STATES PATENT AND TRADEMARK OFFICE
CERTIFICATE OF CORRECTION

PATENT NO. : 5,304,492

DATED : April 19, 1994

INVENTOR(S) : Gary Klinkhammer

It is certified that error appears in the above-identified patent and that said Letters Patent is hereby corrected as shown below:

On the Cover Page:

Item [56], References Cited, U.S. Patent Documents, for U.S. Patent No. 4,929,561, "Hirsh et al." should be --Hirshfeld--.

In the Specification:

Column 1, line 50, a period --.-- should be inserted after "fluorescence" and before "For".

Column 2, line 15, a period --.-- should be inserted after "operations" and before "Even".

Column 2, lines 62-63, a period --.-- should be inserted after "series" and before "The".

Column 2, line 68, a period --.-- should be inserted after "N,N-diethylaniline" and before "The".

Column 4, line 41, "o f" should be --of--.

Column 4, line 46, a period --.-- should be inserted after "supply 16" and before "Socket".

Column 6, line 5, a period --.-- should be inserted after "material" and before "Although".

Column 7, line 26, a period --.-- should be inserted after "Model No. SBE9-02".

Column 7, line 38, a period --.-- should be inserted after "material" and before "The".

Column 7, line 51, "57 inch" should be --0.57 inch--.

Column 9, line 34, a period --.-- should be added after "similar to chlorophyll" and before "Chlorophyll is used".

Column 9, line 65, a period --.-- should be added after "experiments" and before "One".

Column 9, line 67, "de" should be --depths--.

UNITED STATES PATENT AND TRADEMARK OFFICE
CERTIFICATE OF CORRECTION

PATENT NO. : 5,304,492

DATED : April 19, 1994

INVENTOR(S) : Gary Klinkhammer

It is certified that error appears in the above-identified patent and that said Letters Patent is hereby corrected as shown below:

In the Claims:

Column 11, line 9, "optical" should be --optic--.

Column 11, line 12, --first tube which contains a source of-- should be added after the second occurrence of "a" and before "potassium".

Column 12, line 42, "claim 16" should be --claim 14--.

Signed and Sealed this

Ninth Day of February, 1999

Attest:

Attesting Officer

*Acting Commissioner of Patents and Trademarks*